United States Patent [19]

Perkins

[11] 4,123,052
[45] Oct. 31, 1978

[54] TOY OR GAME

[75] Inventor: John A. Perkins, Portage, Mich.

[73] Assignee: Perky & Me Co., Battle Creek, Mich.

[21] Appl. No.: 772,435

[22] Filed: Feb. 28, 1977

[51] Int. Cl.² .............................................. A63J 3/00
[52] U.S. Cl. ..................................... 272/8 N; 46/1 R
[58] Field of Search ................ 46/1 R; 272/8 R, 8 N, 272/137, 139; 128/25 R, 25 B, 133

[56] References Cited

U.S. PATENT DOCUMENTS

| 3,814,419 | 6/1974 | Bjorklund et al. | 272/139 |
| 3,815,904 | 6/1974 | Weiss et al. | 272/137 |

Primary Examiner—Louis G. Mancene
Assistant Examiner—Robert F. Cutting
Attorney, Agent, or Firm—Fisher, Gerhardt & Groh

[57] ABSTRACT

A toy or game is provided which has as an object to increase the lifting power of the forearm. It is particularly attractive to children who wish to demonstrate their ability to lift a dumbbell or other weight by retracting the forearm. It comprises a first sleeve adapted to embrace the forearm and a second sleeve adapted to embrace the upperarm. The sleeves are composed of two halves hinged together so that they can be opened and closed around the arm portion to which they are adapted. Each sleeve has a rigid plastic shell and a soft flexible-foam liner of suitable thickness to form a cushion and to compensate for different size arms. Each sleeve has a groove on the back or underside thereof which is canted toward the other sleeve. These grooves are adapted to receive the ends or bites of an endless elastic band and which, when in place, tends to pull the forearm sleeve toward the upperarm sleeve. The grooves span the unhinged edges of the sleeves, so that when the band is in place, the tension of the band pulls the hinged portions together and effectively latches the sleeves to the arms. An auxiliary friction latch is provided for holding the sleeves in closed position until the elastic bands can be placed in the grooves. A compartment is provided in the forearm sleeve which can hold electronic circuitry or the like.

19 Claims, 7 Drawing Figures

U.S. Patent  Oct. 31, 1978  4,123,052
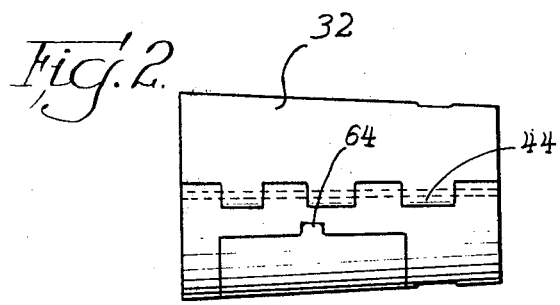
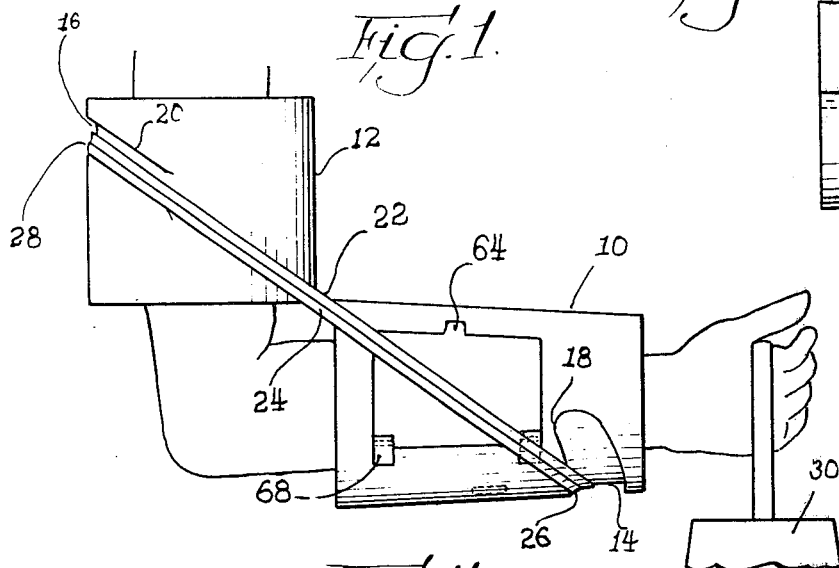
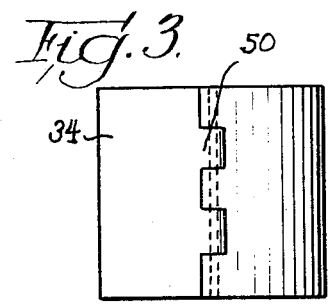
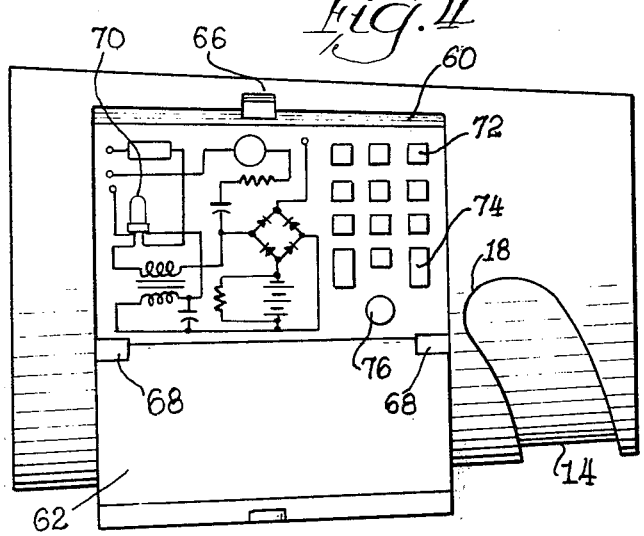
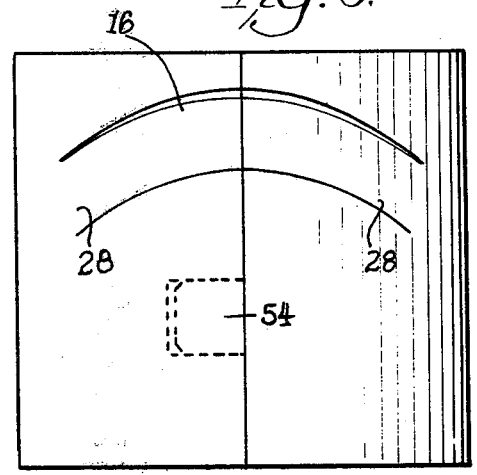
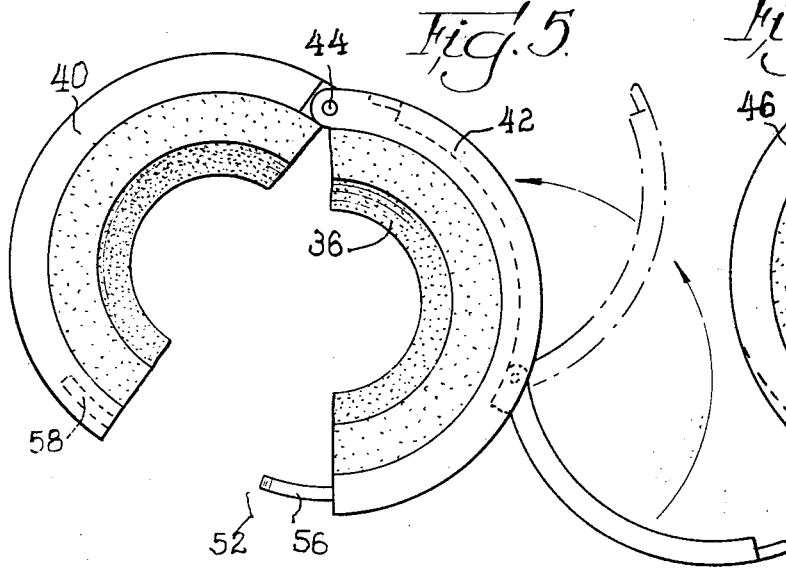
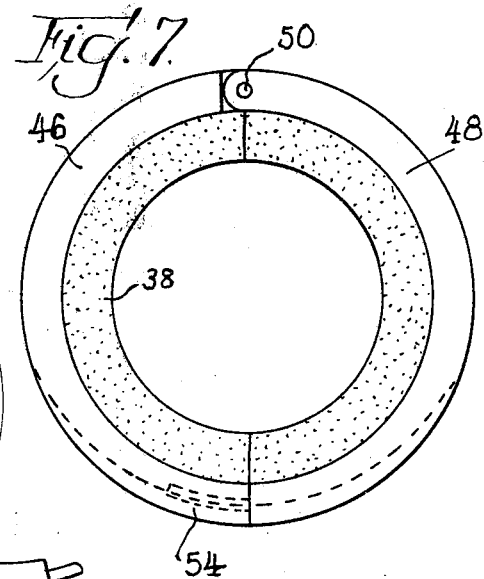

TOY OR GAME

BACKGROUND OF THE INVENTION

FIELD OF INVENTION

This invention relates to a toy or game which can be used by children to enhance their ability to lift dumbells or other objects by retracting the forearm.

Various exercising or prosthetic devices are known in the art in which sleeves are adapted to be attached to the forearm and the upperarm and means is provided for adjusting or modifying the movement of the forearm relative to the upperarm. These devices are, in general, complicated. Some have elaborate means for attaching the upper portion to the shoulder or the back or neck of the individual. None are simple enough in design and construction to be useful as a toy or game device. Some such devices are disclosed in U.S. Pat. Nos. as follows: 886,032; 2,832,334; 2,980,426; 3,288,468; 3,323,518; 3,683,897; 3,698,389; 3,814,419; and, 3,976,057.

OBJECT OF THE INVENTION

It is an object of the invention to provide a new and useful game or toy. It is a further object of the invention to provide a game or toy adapted to augment the muscle-power used in retracting the forearm so as to increase the lifting ability of the forearm. It is a further object of the invention to provide such a device which is simple in construction and simple in operation. It is an object of the invention to provide a device sufficiently simple in construction that it can be manufactured and sold as a toy or a game. It is a further object of the invention to provide a device which is simple enough in construction and operation that it can be handled easily by children. It is an object of the invention to provide a toy or device which avoids the disadvantages of the prior art and which has such advantages as will appear as the description proceeds.

BRIEF DESCRIPTION OF THE INVENTION

The invention relates to a device useful as a game or a toy adapted to augment the muscle-power used in retracting the forearm and to increase the ability of the forearm to lift weights and like objects and is particularly directed to such a device which comprises a first sleeve adapted to embrace the forearm between the wrist and the elbow, first gripping means for causing said first sleeve snugly to embrace the forearm and to deter it from slipping upwardly toward the elbow; a second sleeve adapted to embrace the upperarm between the elbow and the shoulder, second gripping means for causing said second sleeve snugly to embrace the upperarm to deter it from slipping downwardly toward the elbow; and first attaching means on said first sleeve and second attaching means on said second sleeve for attaching an elastic band to said sleeves with one end thereof attached to the first sleeve and the other end thereof attached to the second sleeve in a manner such that the elastic band is placed under tension by the extension of the forearm.

Advantageously, the elastic band is an endless band so that on being stretched there will be a first and second bite at opposite ends and said first and second attaching means are adapted to be engaged by said bites. Also, it is desirable that each sleeve comprise a rigid plastic shell and a soft flexible-foam liner and that the foam liner be thicker than the shell whereby to adapt the sleeves to fit arms of different size children and/or arms of different shapes. Advantageously, attaching means are grooves in the rigid plastic shells, desirably with the grooves in one sleeve being canted toward the other sleeve, and vice versa. Advantageously, each plastic shell comprises hinged portions and means for latching or moving them in arm embracing position. Advantageously, the grooves span the unhinged edges of the sleeve so that when the elastic band is in place in the grooves, the tension of the band will pull the unhinged edges firmly together so that the grooves and elastic band function as an effective latching means. If desired, an auxiliary latching means, preferably of the friction type, can be provided to hold the hinged portions in embracing position until the elastic band is in place.

If desired, a compartment can be provided in the rigid plastic shell with a suitable cover which may be hinged or sliding or snapped in, in which some simulated electronic circuitry can be represented. This makes it possible for the child to pretend that the toy or game is a bionic device and that he can do unusual feats of strength by manipulating push buttons or other devices connected with the simulated circuitry.

It will thus be seen that the device is of such simple and uncomplicated construction that it can be manufactured and sold in the highly competitive toy and game market and that its construction is so simple that even a child can snap the two sleeves on his forearm and upperarm and stretch the rubber band from slot to slot. The device has the further advantage that rubber bands of different strength can be provided so that the device can be adjusted according to the strength and ability of the child. It is contemplated, for example, that the device include two rubber bands, one relatively strong and one relatively weak, so that by using the bands separately or together, three different degrees of tension can be obtained. In a like manner, with three bands of different strengths, six degrees of tension could be obtained.

BRIEF DESCRIPTION OF THE DRAWINGS

In the drawings:

FIG. 1 is a side elevation showing the device of the invention in use.

FIG. 2 is a side elevation of the forearm sleeve.

FIG. 3 is a side elevation of the upperarm sleeve.

FIG. 4 is a side elevation of the forearm sleeve showing a compartment with simulated electronic circuitry therein.

FIG. 5 is an end view of the forearm sleeve with parts in open position.

FIG. 6 is a rear elevation of the forearm sleeve.

FIG. 7 is a top or end elevation of the forearm sleeve.

DETAILED DESCRIPTION OF THE INVENTION

Referring now particularly to FIG. 1 there will be seen a first or forearm sleeve 10 adapted snugly to embrace the forearm as shown and an upperarm sleeve 12 adapted snugly to embrace the upperarm as shown. The lower arm sleeve 10 has a slot 14 and the upperarm sleeve 12 has a slot 16. The slot 14 is canted as shown at 18 toward the upperarm sleeve and the slot 16 is canted at 20 toward the forearm sleeve. The slots 20 and 16 constitute means for attaching an elastic band or bands 22 and 24 to the sleeves 10 and 12.

The bands 22 and 24 are endless bands so that when stretched from one slot to the other, there is a bite 26 formed at one end and a bite 28 formed at the other, which bites seat, respectively, in the slots 14 and 16.

The bands 22 and 24 place the two sleeves under tension so that the bands constantly urge the forearm to the retracted position. As a consequence, when the forearm is extended and a weight 30 is grasped, the child can lift the weight to a position shown in FIG. 1 with greater than ordinary ease.

The sleeves are constructed with an outer shell 32 and 34 of rigid plastic material, 36 and 38 of soft flexible-foam. Any rigid plastic, such as nylon, polystyrene, polypropylene, polycarbonate, and the like can be used. Also, any standard soft flexible foam, such as foam rubber or flexible polyurethane foam, can be used.

The rigid outer shell of the forearm sleeve is composed of two sections 40 and 42 which are semi-circular in cross-section and are hinged at 44, so that they can be opened to the position shown for applying the sleeve to the forearm and then closed to give a sleeve having a circular cross-section.

The upperarm sleeve, similarly, has a portion 46 and a portion 48 hinged together at 50 which likewise have a similar cross-section, so that when the sleeve is in the closed position as shown in FIG. 7, it has a circular cross-section.

The soft flexible-foam liners 36 and 38 are complementary to the outer shell portions 40, 42, 46, and 48, and are bonded thereto. The liners have a thickness relatively greater than the thickness of the outer shell to provide good cushioning and to compensate for different size arms. The sleeves shown in FIGS. 5 and 7, particularly, are provided with friction latches 52 and 54, which comprises a male portion 56 projecting from an unhinged edge of the rigid portion 42 adapted to be received into a complementary female portion in the opposite edge of the rigid portion 40. The male portion or tongue 56 is of such size as compared with the female or slot portion 58 that when the two unhinged edges are brought together, the male portion or tongue 56 will be frictionally engaged in the female portion or slot 58.

As best shown in FIGS. 4 and 5, the forearm sleeve is in the shape of a truncated cone, tapering from one end to the other, the better to adapt it to the shape of the forearm. On the other hand, the upperarm sleeve is in the shape of a cylinder, better to accommodate it to the upperarm.

The forearm sleeve is provided with a compartment 60, provided with a cover 62 having a latch means 64-66. The cover is hinged at 68. Within the compartment 60 is a simulated electronic circuitry 70, together with a multiplicity of push-buttons 72, 74, and 76, having different sizes and shapes. Thus, in playing with the toy or the game, the child can pretend he has a "bionic arm" and that by manipulating the various push-buttons 72, 74, and 76, he can adjust the circuit to adjust the power of the arm. In actual practice, this is done by providing in the kit at least two elastic bands 22 and 24, one of which is stronger than the other. Thus, if only the weak band 22 is in place, the increase in lifting ability is minimal. When both bands are in place, the lifting ability is maximal and if only the stronger band 24 is in place, the increase in lifting ability is intermediate. By including in the kit three elastic bands of three different strengths, six different degrees of increase in lifting ability is obtainable.

It is to be understood that the invention is not to be limited to the exact details of operation or structure shown and described, as obvious modifications and equivalents will be apparent to one skilled in the art.

I claim:

1. A device useful as a game or toy adapted to augment the muscle-power used in retracting the forearm, comprising a first sleeve adapted to embrace the forearm between the wrist and the elbow, first gripping means for causing said first sleeve snugly to embrace the forearm and to prevent it from slipping upwardly toward the elbow, a second sleeve adapted to embrace the upperarm between the elbow and the shoulder, second gripping means for causing said second sleeve snugly to embrace the upperarm and to prevent it from slipping downwardly toward said elbow, and first attaching means on said first sleeve and second attaching means on said second sleeve for attaching an elastic band to said sleeves with one end attached to the first attaching means and the other end attached to the second attaching means in a manner such that the elastic band is placed under tension by the extension of the forearm.

2. The device of claim 1, in which said elastic band is an endless band, so that on being stretched, there will be a first bite and a second bite at opposite ends thereof and said first attaching means and said second attaching means are adapted to be engaged by said bite.

3. The device of claim 1, in which each said sleeve comprises a rigid plastic shell and a soft flexible-foam liner.

4. The device of claim 3, in which said liner is relatively thick compared with said shell, whereby the sleeves are adapted to fit the arms of different size children.

5. The device of claim 3, in which said elastic band is an endless band, so that on being stretched, there will be a first bite and a second bite at opposite ends thereof and said first attaching means and said second attaching means are adapted to be engaged by said bite.

6. The device of claim 5, in which said first attaching means comprises a first groove in said rigid plastic shell of said first sleeve on the underside thereof and said second attaching means comprises a second groove in said rigid plastic shell on said second sleeve on the backside thereof.

7. The device of claim 6, in which the first groove is canted toward said second sleeve and said second groove is canted toward said first sleeve.

8. The device of claim 7, in which said liner is relatively thick compared with said shell, whereby the sleeves are adapted to fit the arms of different size children.

9. The device of claim 3, in which each plastic shell comprises hinged portions and first latching means for latching the unhinged edges of said first sleeve together in forearm embracing position and second latching means for holding the unhinged edges of said second sleeve together in upperarm embracing position.

10. The device of claim 9, in which said elastic band is an endless band, so that on being stretched, there will be a first bite and a second bite at opposite ends thereof and said first attaching means and said second attaching means are adapted to be engaged by said bite.

11. The device of claim 10, in which said first latching means spans the unhinged edges of said first sleeve and said second latching means spans the unhinged edges of said second sleeve, whereby when the bites of said elastic band are placed in engagement with said attaching means, it also functions as latching means to hold said hinged portions in embracing position.

12. The device of claim 11, in which said hinged edges comprise an auxiliary latching means to hold the hinged sections in embracing position until the elastic band is in place.

13. The device of claim 12, in which the auxiliary latching means is a friction latch.

14. The device of claim 11, in which said first attaching means comprises a first groove in said rigid plastic shell of said first sleeve on the underside thereof and said second attaching means comprises a second groove in said rigid plastic shell on said second sleeve on the backside thereof.

15. The device of claim 14, in which each groove spans the unhinged edges.

16. The device of claim 15, in which the first groove is canted toward said second sleeve and said second groove is canted toward said first sleeve.

17. The device of claim 16, in which said liner is relatively thick compared with said shell, whereby the sleeves are adapted to fit the arms of different size children.

18. The device of claim 17, in which said hinged edges comprise an auxiliary latching means to hold the hinged sections in embracing position until the elastic band is in place.

19. The device of claim 18, in which the auxiliary latching means is a friction latch.

* * * * *